United States Patent [19]
Fleischaker

[11] Patent Number: 5,447,167
[45] Date of Patent: Sep. 5, 1995

[54] HAND PRESSURE LEVEL THRESHOLD SENSOR

[76] Inventor: William J. Fleischaker, P.O. Box 1178, Oklahoma City, Okla. 73101

[21] Appl. No.: 96,990
[22] Filed: Jul. 27, 1993
[51] Int. Cl.⁶ .............................................. A61B 5/103
[52] U.S. Cl. ................................................... 128/782
[58] Field of Search .................. 128/774, 782; 73/862, 73/865.4

[56] References Cited

U.S. PATENT DOCUMENTS

| 4,337,780 | 7/1982 | Metrick | 128/774 |
| 4,949,729 | 8/1990 | Haski | 128/782 |
| 5,174,154 | 12/1992 | Edwards | 128/774 |

FOREIGN PATENT DOCUMENTS 1525259 9/1978 United Kingdom ................ 128/782

Primary Examiner—Max Hindenburg
Attorney, Agent, or Firm—Joseph W. Mott

[57] ABSTRACT

A hand pressure threshold sensor generates a signal representative of the application of excessive force to a hand held instrument to which the sensor is coupled. By using the sensor, a person having impaired tactile sensibilities, such that he is unaware of the degree of force he is applying, an instrument may be alerted that he is applying excess force. By reducing the force being applied to the implement, the person will avoid harming his hand or the implement as a result of his unknowing application of excessive force. The sensor may be provided with a threshold which outputs a signal representative of inadequate grasping force as well. A dedicated sensor may be incorporated directly within an implement, for example a fountain pen. A portable sensor may be utilized with a variety of hand held implements.

8 Claims, 1 Drawing Sheet

HAND PRESSURE LEVEL THRESHOLD SENSOR

BACKGROUND

1. Technical Field of the Invention

The invention relates to a pressure threshold sensor for sensing when hand pressure applied to a hand held implement exceeds a desired level. In particular, the invention relates to a pressure threshold alarm for alerting an individual having an impaired sense of feel in the hand, that they are applying excessive pressure in grasping an instrument and should release that pressure in order to avoid damaging their hand.

2. Prior Background Art

A person may lose a sense of feeling in his extremities and still be able to walk and manipulate hand held items. There may be many causes for such a condition, one of the most notorious being Hansen's Disease. Hansen's Disease is more familiarly known as Leprosy. However, a person does not have to suffer a life threatening infliction to have impaired tactile function of the hands; an injury or operation can result in such a problem.

A person suffering such impairment of their tactile senses may understandably hurt themselves when their hand or foot impacts on an object or they strike a projection or a sharp edge and cut themselves. It is a little known fact, however, that a person whose tactile senses are impaired can harm themselves or an object by the manner in which they grasp the object.

In applying pressure to an object, for example a simple fountain pen or the like, a person with impaired tactile sense will grasp the item with sufficient pressure to prevent it slipping from his grasp. However, in the course of using the object, or implement, the person's grip tends to unconsciously increase. The person has little or no tactile feedback to The portable sensor also includes second means for initiating a second signal output from the hand pressure sensor when the hand gripping pressure applied to the sensor is less than a second selected pressure level.

The invention is also claimed as a hand pressure sensor for use with a hand held implement by a person whose tactile senses are impaired, the sensor being produced by the process steps of:

selecting a pressure sensor which outputs a signal representative of the pressure applied to the sensor when the sensor is grasped by a person's hand;

providing the sensor with means for inhibiting the output of the signal until the pressure induced by grasping the sensor exceeds a selected value;

coupling the sensor to a first selected hand held implement to be grasped by a person's hand as the person's hand grasps the implement;

providing sensible signal means for outputting a sensible signal responsive to the signal output by the sensor; and coupling the output signal from the sensor to the sensible signal means.

Further process steps contributing to the innovative device include selecting the hand held implement to be a pen; and coupling the sensible signal means to the pen.

The process step of coupling the sensor to a first selected hand held implement may further comprise the step of removable coupling the sensor to the first selected implement; and the process steps include the further steps of: removing the sensor from the first selected implement; and removably coupling the sensor to a second selected hand held implement.

DETAILS OF BEST MODE FOR CARRYING OUT THE INVENTION

Figure 1:
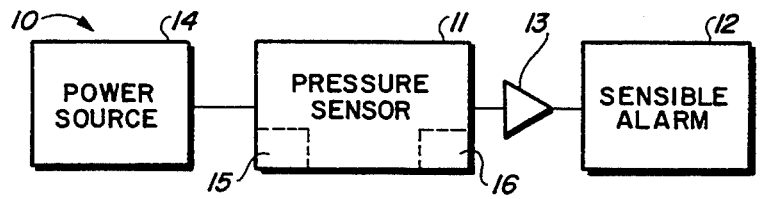
FIG. 1 is a block diagram of the hand pressure threshold sensor disclosed herein.

For purposes of promoting an understanding of the principles of the invention, reference will now be made to the embodiments illustrated in the drawings and specific language will be used to describe same. It will nevertheless be understood that no limitation of the scope of the invention is thereby intended. Alterations and modifications of the illustrated device are contemplated, as are such further applications of the principles of the invention as would normally occur to one skilled in the art to which the invention pertains.

The invention herein disclosed is a hand pressure threshold sensing system 10 illustrated in block diagram form in FIG. 1. Threshold sensor 10 includes a pressure sensor 11 which outputs a signal to a sensible alarm 12. Sensible alarm 12 may be an audible alarm or, preferably, a visual alarm. The signal output by pressure sensor 11 may be amplified by amplifier 13 if required to operate sensible alarm 12. Sensor 11 is provided with a threshold set 15 which inhibits a signal output from pressure sensor 11 until a pressure exceeding a selected threshold level is reached or exceeded. When the selected pressure level is reached or exceeded, sensor 11 outputs a signal to sensible alarm 12 to alert the user that his hand is exerting too great a pressure on the implement to which the system 10 is coupled.

Although, in most cases, a person with impaired tactile senses will be aware if an implement in her grasp begins to slip from that grasp, it may be advisable to alert the person prior to any slippage of an implement from his grasp. To this end a lower threshold limit set 16 may be utilized to set the low threshold level at which a second signal is output from pressure sensor 11. This second signal will be representative of a hand pressure which is close to being insufficient to properly grasp the implement in hand. Where both threshold limits 15 and 16 are functional, the signal output by sensible alarm 12 will vary in a manner so as to distinguish the low level output signal of sensor 11 from the high level threshold signal.

A power source is provided to power the sensors 11, alarm 12, and amplifier 13. In all probability, the power source is battery. However, a thermally actuated sensor is envisioned in which the color of the sensor itself changes color as the temperature of the person's fingers varies with her grasp. As a person's grasp increases and becomes extreme, blood circulation through the fingers decreases. Finger temperature is reduced thereby.

By making the sensor of the same material now used as a skin surface contact, temperature indicating band wherein the band changes color with temperature, a person may observe the color change of the sensor, induced by reduced blood circulation in the fingers, and loosen his grip. The improved blood circulation will then warm the fingers and return the sensor to a "safe" color. The thermal color change is selected to be representation of selected hand grasping pressure levels.

Figure 2:
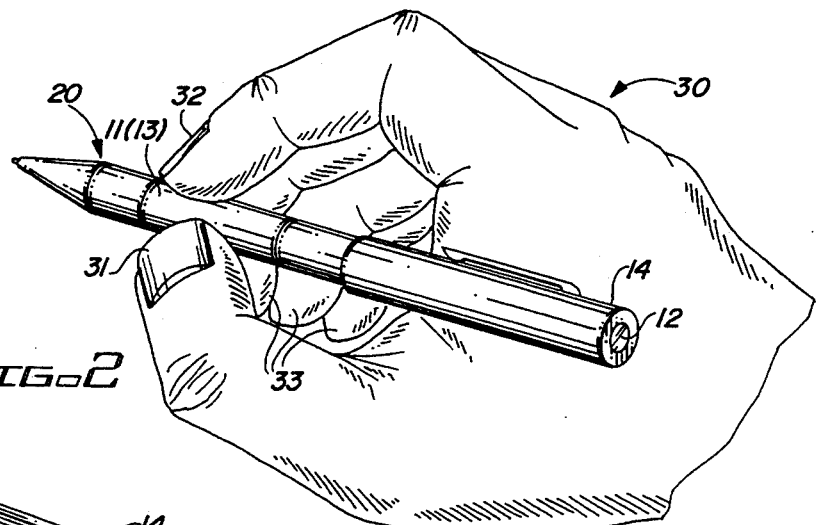
FIG. 2 is a perspective view of a person's hand holding a fountain pen in which the hand pressure threshold sensor of FIG. 1 has been incorporated.

In FIG. 2 is illustrated a fountain pen 20 in the grasp of a hand 30. Pressure is applied to the fountain pen by thumb 31, index finger 32, and second finger 33. Pressure sensor 11 and any necessary amplifying device 13 is incorporated into the barrel of pen 20 so that the grasp of fingers 31–33 exerts their pressure on pressure sensor 11. At the rightmost end of pen 20, in the illustration of FIG. 2, is shown power source 14 and sensible signal 12, represented in the drawing as a light emitting signal. When a person having impaired tactile sense grasps pen 20 in his hand 30, the pressure of his fingers 31–32 on sensor 11 will cause a signal to be output from sensor 11 if the pressure of those fingers exceeds a pre-selected level established by threshold 15 within pressure sensor 11. When this threshold level is exceeded a signal is output from sensor 11 causing the sensible alarm 12 to light so as to call attention of the user to the fact that he is exerting too much pressure on the pen in the region of sensor 11. When the user eases the pressure induced by his grasp of the pen, the visual signal output by alarm 12 is extinguished. Should the user release his grasp to such an extent that the pen may be expelled from between his fingers the setting of threshold 16 will provide a signal at 12 indicative that insufficient pressure is being applied.

Not shown in the drawings but well known and understood to those skilled in the art will be means for actuating the system. Actuation may be achieved upon initially grasping pressure sensor 11.

Figure 3:
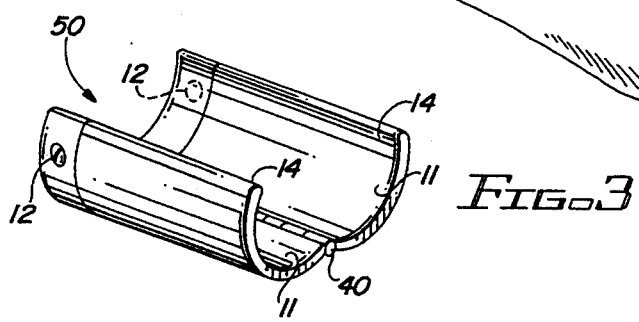
FIG. 3 is a conceptual, perspective illustration of a portable, hand pressure threshold sensor which may be utilized with a variety of hand held implements.

In the embodiment of the device shown in FIG. 3, the invention is represented as a portable, hand pressure threshold sensor 50. It is intended that threshold sensor 50 will be utilized with a variety of hand held implements. To this end, pressure sensors 11 are coupled together by means of, for example hinge 40. Sensors 11 then form an adjustable sheath which may be used to partially encompass the handle of a hand held implement. A power source 14, shown here as a battery operated power source, is incorporated in portable sensor 50 as are sensible alarms 12, represented here as light emitting sources.

Figure 4:
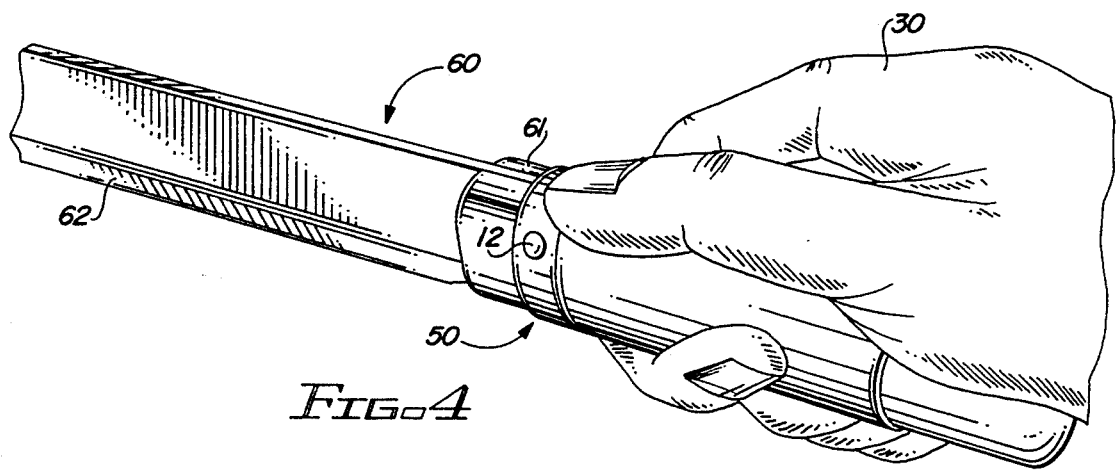
FIG. 4 illustrates the use of the portable, hand pressure threshold sensor of FIG. 3 utilized by a person in grasping a handle of a carving knife.

The portable sensor 50 is used in the manner illustrated in FIG. 4 wherein sensor 50 has been placed so as to encompass handle 61 of knife 60. When a tactilly deprived person utilizes his hand 30 to hold knife handle 61, his grasp of sensor 50, if excessive, will cause signals 12 to emit a visual signal. The person may then, as before, ease his grasp on sensor 15 thereby easing his grasp of handle 61. To prevent the danger of knife blade 62 from slipping due to an inadequate grasp, the low level threshold 16 may be relied upon to cause the emission of a visual signal at alarm 12 indicative of an inadequate grasping pressure.

What has been disclosed is a hand pressure threshold sensor for generating a signal representative of the application of excessive force to a hand held instrument to which the sensor is coupled. By using the sensor, a person having impaired tactile sensibilities, such that he is unaware of the degree of force he is applying, an instrument may be alerted that he is applying excess force. By reducing the force being applied to the implement, the person will avoid harming his hand or the implement as a result of his unknowing application of excessive force. The sensor may be provided with a threshold which outputs a signal representative of inadequate grasping force as well. A dedicated sensor may be incorporated directly within an implement, for example a fountain pen. A portable sensor may be utilized with a variety of hand held implements.

Those skilled in the art will conceive of other embodiments of the invention which may be drawn from the disclosure herein. To the extent that such other embodiments are so drawn, it is intended that they shall fall within the ambit of protection provided by the claims herein.

tion and drawings in such clear and concise manner that those skilled in the art may readily understand and practice the invention, That which is claimed is:

1. A hand pressure sensor for use with a hand held implement useful for performing a task other than hand gripping pressure measurement, said sensor comprising:
a hand held implement; and
a hand pressure sensor for outputting a first signal representative of the hand gripping pressure applied to said sensor, said sensor including first means for initiating said first signal when said hand gripping pressure applied to said sensor exceeds a first selected pressure level;
said sensor being coupled to said implement to be grasped as a person uses said implement.

2. The sensor of claim 1 further including second means for initiating second signal output from said hand pressure sensor when said hand gripping pressure applied to said sensor is less than a second selected pressure level.

3. The sensor of claim 1 said hand held implement being a manual writing instrument.

4. The sensor of claim 3 said writing instrument being a pen.

5. The sensor of claim 1 said hand pressure sensor being portable and having means for removably coupling said sensor to said hand held implement, said sensor being adapted to be removably coupled to selected ones of a plurality of varied hand held implements.

6. The sensor of claim 5 further including second means for initiating second signal output from said hand pressure sensor when said hand gripping pressure applied to said sensor is less than a second selected pressure level.

7. The sensor of claim 5 said hand held implement being a manual writing instrument.

8. The sensor of claim 7 said writing instrument being a pen.

* * * * *